United States Patent
Boylan et al.

(10) Patent No.: US 11,326,132 B2
(45) Date of Patent: *May 10, 2022

(54) ANTIMICROBIAL NONWOVEN WET WIPE BONDED WITH A NONIONIC BINDER

(71) Applicants: WACKER CHEMIE AG, Munich (DE); John Richard Boylan, Bethlehem, PA (US)

(72) Inventors: John Richard Boylan, Bethlehem, PA (US); Dennis Sagl, Fogelsville, PA (US)

(73) Assignee: Wacker Chemie AG, Munich (DE)

( * ) Notice: Subject to any disclaimer, the term of this patent is extended or adjusted under 35 U.S.C. 154(b) by 204 days.

This patent is subject to a terminal disclaimer.

(21) Appl. No.: 16/610,635

(22) PCT Filed: May 3, 2017

(86) PCT No.: PCT/US2017/030787
§ 371 (c)(1),
(2) Date: Nov. 4, 2019

(87) PCT Pub. No.: WO2018/203890
PCT Pub. Date: Nov. 8, 2018

(65) Prior Publication Data
US 2020/0056124 A1    Feb. 20, 2020

(51) Int. Cl.
| | | |
|---|---|---|
| *C11D 1/62* | (2006.01) | |
| *C11D 1/72* | (2006.01) | |
| *C11D 1/835* | (2006.01) | |
| *C11D 3/22* | (2006.01) | |
| *C11D 3/30* | (2006.01) | |
| *C11D 3/37* | (2006.01) | |
| *C11D 3/48* | (2006.01) | |
| *A01N 25/34* | (2006.01) | |
| *A01N 33/12* | (2006.01) | |
| *D04H 1/587* | (2012.01) | |
| *D04H 1/64* | (2012.01) | |
| *A61K 8/39* | (2006.01) | |
| *C11D 1/722* | (2006.01) | |
| *C11D 17/04* | (2006.01) | |

(52) U.S. Cl.
CPC ............... *C11D 3/48* (2013.01); *C11D 1/62* (2013.01); *C11D 1/722* (2013.01); *C11D 1/835* (2013.01); *C11D 3/225* (2013.01); *C11D 3/3749* (2013.01); *C11D 3/3753* (2013.01); *C11D 17/049* (2013.01); *D04H 1/587* (2013.01); *D04H 1/64* (2013.01)

(58) Field of Classification Search
CPC .. C11D 1/62; C11D 1/72; C11D 1/662; C11D 1/835; C11D 3/22; C11D 3/30; C11D 3/37; C11D 3/3753; C11D 3/3757; C11D 3/48; C11D 17/049; A01N 25/34; A01N 33/12; D04H 1/587; D04H 1/64; A61Q 17/005; A61K 8/0208; A61K 8/39; A61K 8/416; A61K 8/731; A61K 8/8129
See application file for complete search history.

(56) References Cited

U.S. PATENT DOCUMENTS

| | | | |
|---|---|---|---|
| 4,449,978 A | 5/1984 | Iacoviello | |
| 4,741,944 A * | 5/1988 | Jackson | A61F 13/00991 15/104.93 |
| 5,109,063 A | 4/1992 | Cheng et al. | |
| 7,915,184 B2 | 3/2011 | Ellis et al. | |
| 2002/0031486 A1 | 3/2002 | Lunsmann et al. | |
| 2002/0183233 A1 | 12/2002 | Mitra et al. | |
| 2012/0028527 A1* | 2/2012 | Boylan | D04H 1/587 442/155 |

FOREIGN PATENT DOCUMENTS

JP    2012197250 A    10/2012

OTHER PUBLICATIONS

Polym et al., "Effect of colloid stabilizer on vinyl acetate copolymer emulsion and membrane", Progress in Fine Petrochemical Industry, Mar. 15, 2000, p. 55-56. China Academic Journal Electronic Publishing House.
T. G. Fox, "Influence of Diluent and of Copolymer Composition on the Glass Temperature of a Polymer System", The Bulletin of the American Physical Society, 1956, p. 123, vol. 1, College Park, MD, US.
J. Brandrup et al., Polymer Handbook Second Edition, 1975, pp. 111-170, John Wiley & Sons, New York, US.

* cited by examiner

*Primary Examiner* — Brian P Mruk
(74) *Attorney, Agent, or Firm* — Brooks Kushman P.C.

(57) ABSTRACT

An antimicrobial nonwoven wet wipe includes i) a fibrous nonwoven substrate bonded with a cross-linkable VAE dispersion stabilized with one or more nonionic colloidal stabilizers and one or more nonionic surfactants, and ii) absorbed in the nonwoven substrate, an aqueous lotion including one or more cationic disinfectants. No anionic surfactants are present in the antimicrobial nonwoven wet wipe. A method of producing the antimicrobial nonwoven wet wipe includes a) applying a first aqueous composition including a crosslinkable VAE dispersion stabilized with one or more nonionic colloidal stabilizers and one or more nonionic surfactants to a nonwoven substrate; b) drying the composition; and c) applying a second aqueous composition to the product of step b). At least one of the first and second aqueous compositions includes one or more cationic disinfectants.

17 Claims, No Drawings

ANTIMICROBIAL NONWOVEN WET WIPE BONDED WITH A NONIONIC BINDER

CROSS REFERENCE TO RELATED APPLICATIONS

This application is the U.S. National Phase of PCT Appln. No. PCT/EP2017/030787 filed May 3, 2017, the disclosure of which is incorporated in its entirety by reference herein.

BACKGROUND OF THE INVENTION

1. Field of the Invention

The invention relates to a nonwoven wet wipe comprising an aqueous antimicrobial lotion, in which the wipe is bonded with a nonionic binder.

2. Description of the Related Art

Self-crosslinking dispersion binders for the airlaid nonwovens industry are typically stabilized with some amount of anionic surfactant(s). U.S. Pat. No. 5,109,063 discloses a process for making a vinyl acetate ethylene N-methylol acrylamide (NMA) copolymer emulsion for nonwoven binder applications. The emulsifying system consists of a salt of an alkyleneoxy poly(ethyleneoxy)sulfate. Binders of this type are commonly utilized in lotionized wet wipe applications where the lotion is compatible with the anionic nature of the self-crosslinking binder used to provide integrity to the nonwoven article. U.S. Pat. No. 7,915,184 claims a nonwoven antimicrobial wipe comprising a fibrous nonwoven substrate coated with a nonionic and cationic binder mixture and subsequently coated with a cationic disinfectant. U.S. Pat. No. 4,449,978 claims a dry nonwoven product which is bonded with an interpolymer of vinyl acetate, ethylene, NMA and acrylamide stabilized with a nonionic emulsifying agent.

US 2002/0183233 A1 discloses an improvement of antimicrobial nonwoven wipes by the addition of a salt to the lotion, which improves the release of the cationic disinfectant. There remains a need for a simple and cost-effective way for improving the efficacy of cationic disinfectants in wet wipe compositions.

US 2002/0031486 A1 discloses wet wipes impregnated with an antimicrobial cleansing composition comprising an antimicrobial agent and a nonionic surfactant. JP 2012-197250 A discloses sheet-like cosmetics impregnated with a liquid composition containing a cationic disinfectant, a nonionic surfactant, a cationic polymer, and ethanol.

SUMMARY OF THE INVENTION

The invention provides an antimicrobial nonwoven wet wipe that includes i) a fibrous nonwoven substrate bonded with a cross-linkable VAE dispersion stabilized with one or more nonionic colloidal stabilizers and one or more nonionic surfactants, and ii) absorbed in the nonwoven substrate, an aqueous lotion including one or more cationic disinfectants. No anionic surfactants are present in the antimicrobial nonwoven wet wipe. The antimicrobial nonwoven wet wipes are produced by a method which includes a) applying a first aqueous composition including a crosslinkable VAE dispersion stabilized with one or more nonionic colloidal stabilizers and one or more nonionic surfactants to a nonwoven substrate; b) drying the composition; and c) applying a second aqueous composition to the product of step b). At least one of the first and second aqueous compositions includes one or more cationic disinfectants.

DETAILED DESCRIPTION OF THE PREFERRED EMBODIMENTS

The inventors have found that the release, and therefore the efficacy, of cationic disinfectants, for example quaternary ammonium disinfectants, is diminished if anionic surfactants are present in a nonwoven wet wipe. Anionic surfactants are commonly used to stabilize vinyl acetate ethylene copolymer (VAE) dispersions used as binders for nonwoven substrates. However, the inventors have found that VAE dispersions that are nonionically stabilized with a combination of one or more nonionic surfactants and one or more nonionic protective colloids provide improved efficacy of the cationic disinfectant in wet wipe compositions compared with anionically stabilized VAE binder dispersions. The binder compositions according to the invention, and the wet wipes produced from them, are therefore free, or essentially free, of anionic surfactants so as to avoid interfering with the activity of the cationic disinfectant. Preferably, the antimicrobial nonwoven wet wipes do is not include polymers comprising multiple cationic moieties.

Components and methods of making antimicrobial nonwoven wet wipes bonded with nonionic VAE binders according to the invention will now be discussed in detail. Unless the context indicates otherwise, percentages of materials recited herein are by weight.

VAE Copolymer

Unless specified otherwise, percentages by weight of monomers mentioned herein are based on the total weight of all monomers used for the polymerization to make the VAE copolymer, with the weight percentages of the monomers summing in each case to 100%. Similarly, monomer percentages in a copolymer are reported on a weight basis.

VAE copolymers for use as binders according to the invention comprise polymerized units of vinyl acetate, ethylene, an N-methylol-functional monomer, and (meth)acrylamide, i.e., acrylamide and/or methacrylamide. Vinyl acetate is copolymerized in general in an amount of at least 65% by weight, or at least 70%, and at most 94.5% by weight, or at most 85%.

Ethylene is copolymerized in general in an amount of at least 5% by weight, or at least 10%, and at most 30% or at most 20% by weight.

The fraction of the N-methylol-functional monomer in the copolymer is typically at least 0.1% by weight, or at least 0.5%, 1%, or 2% by weight, and is typically at most 10.0% by weight, or at most 8%, or 5% by weight, based in each case on the total weight of monomers used for the polymerization.

Suitable amounts of N-methylol-functional monomer, relative to the total of N-methylol-functional monomer plus (meth)acrylamide, are at least 25% by weight, or at least 30%, 35%, 40%, 45%, 50%, or 55% by weight. The amount will be at most 85%, or at most 80%, 75%, 70%, 65%, or 60% by weight.

The total amount of N-methylol-functional monomer plus (meth)acrylamide present in the copolymer is at least 0.2% by weight, or at least 0.5%, 1%, 3%, or 5% by weight, and at most 5.0% by weight, or at most 8%, 10%, or 15% by weight.

Suitable exemplary N-methylol-functional monomers for making the copolymer include N-methylolacrylamide (NMA), N-methylolmethacrylamide, allyl N-methylolcarbamate, and esters of N-methylolacrylamide, N-methylolmethacrylamide, or of allyl N-methylolcarbamate. N-methylolacrylamide and N-methylol-methacrylamide are particularly preferred. The N-methylol-functional monomer is used in combination with acrylamide and/or methacrylamide, preferably in combination with acrylamide. Most preferred are blends of N-methylolacrylamide and acrylamide. Such blends are commercially available, for example being a 48% aqueous solution of NMA and acrylamide in a 1:1 molar ratio, available under the tradename CYLINK® NMA-LF MONOMER (Cytec Industries, Woodland Park, N.J.), or an aqueous solution containing 28% b.w. N-methylolacrylamide and 20% b.w. acrylamide, available under the tradename FLOCRYL® NMA 2820 (SNF Floerger, Andrezieux, France). Alternatively, the NMA and acrylamide may be added separately to the polymerization feed.

In addition to NMA, other N—($C_{1-4}$) alkylol (meth) acrylamides may be included in the VAE copolymer. Olefinically unsaturated monomers containing cellulose-reactive moieties may also be included, for example those containing aldehyde, protected aldehyde, and glycolic acid moieties. Examples include i-butoxymethylacrylamide, acrylamidoglycolic acid, acrylamidobutyraldehyde, and dialkyl acetals of acrylamidobutyraldehyde in which the alkyl groups each individually have 1 to 4 carbon atoms.

Optionally, the range of available properties for the copolymer in the dispersion may be extended by including additional monomers in the VAE copolymer. Typically, suitable comonomers are monomers with a single polymerizable olefinic group. Examples of such comonomers are vinyl esters of carboxylic acids having 3 to 18 C atoms. Preferred vinyl esters are vinyl propionate, vinyl butyrate, vinyl 2-ethylhexanoate, vinyl laurate. 1-methyl vinyl acetate, vinyl pivalate, and vinyl esters of α-branched monocarboxylic acids having 9 to 11 C atoms, examples being VEOVA9™ or VEOVA10™ esters (available from Momentive Specialty Chemicals, Houston, Tex.). Other suitable comonomers include esters of acrylic acid or methacrylic acid with unbranched or branched alcohols having 1 to 15 C atoms. Exemplary methacrylic esters or acrylic esters include methyl acrylate, methyl methacrylate, ethyl acrylate, ethyl methacrylate, propyl acrylate, propyl methacrylate, n-butyl acrylate, n-butyl methacrylate, 2-ethylhexyl acrylate and norbornyl acrylate. Other suitable comonomers include vinyl halides such as vinyl chloride, or olefins such as propylene. In general the further comonomers are copolymerized in an amount of 0.5 to 30% by weight, preferably 0.5 to 20% by weight, based on the total weight of monomers used for the polymerization.

Optionally, 0.05 to 10% by weight, based on the total weight of monomers used for the polymerization, of other monomers (auxiliary monomers) may additionally be copolymerized in forming the dispersion. Auxiliary monomers include a polymerizable olefinic group and at least one additional functional group. Examples of auxiliary monomers include acrylonitrile and diesters of fumaric acid and maleic acid, for example the diethyl and diisopropyl esters. Typically, there is only one polymerizable olefinic group in each monomer used to make the VAE copolymer, although in some cases there may be more.

On the other hand, ethylenically unsaturated monomers that contain carboxylic acid, sulphonic acid, or phosphate or phosphonate acid groups, salts of these, or groups that hydrolyze to these when used to make wet wipes according to the invention, are typically excluded from VAE copolymers used as binders to make the wipes. More generally, polymers of any sort comprising any or all of these as monomer units may be excluded from the wet wipes of the invention. Specific examples include acrylic acid, methacrylic acid, fumaric acid, maleic acid, maleic anhydride, vinylsulphonic acid, and 2-acrylamido-2-methyl-propane-sulphonic acid.

The choice of monomers or the choice of the proportions by weight of the monomers is preferably made in such a way that, in general, the copolymer has a suitable glass transition temperature (Tg). Typically, the Tg is at least −10° C., or at least −5° C., or at least 0° C., and at most +20° C., or at most +15° C., or at most +10° C. The glass transition temperature Tg of the is copolymers can be determined in a known way by means of differential scanning calorimetry (DSC) with a heating rate of 10° K per minute according to ASTM D3418-82 as onset temperature. The Tg can also be calculated approximately beforehand by means of the Fox equation. According to Fox T. G., Bull. Am. Physics Soc. 1, 3, page 123 (1956): $1/Tg=x1/Tg1+x2'Tg2+ \ldots +xn/Tgn$, where xn is the mass fraction (% by weight/100) of the monomer n and Tgn is the glass transition temperature in kelvin of the homopolymer of the monomer n. Tg values for homopolymers are given in the Polymer Handbook 2nd Edition, J. Wiley & Sons, New York (1975).

Nonionic Surfactant

Suitable nonionic surfactants, also referred to herein as nonionic emulsifiers are, for example, acyl, alkyl, oleyl, and alkylaryl ethoxylates. Also suitable are ethoxylated branched or unbranched fatty alcohols (aliphatic alcohols), preferably having a degree of ethoxylation of 3 to 80 ethylene oxide units and $C_6$ to $C_{36}$ alkyl radicals. Other examples include $C_{13}$-$C_{15}$ oxo-process alcohol ethoxylates having a degree of ethoxylation of 3 to 30 ethylene oxide units, $C_{16}$-$C_{18}$ fatty alcohol ethoxylates having a degree of ethoxylation of 11 to 80 ethylene oxide units, $C_{10}$ oxo-process alcohol ethoxylates having a degree of ethoxylation of 3 to 11 ethylene oxide units, $C_{13}$ oxo-process alcohol ethoxylates having a degree of ethoxylation of 3 to 20 ethylene oxide units, polyoxyethylenesorbitan monooleate having 20 ethylene oxide groups. Additional examples include polyethylene oxide ethers of oleyl alcohol, having a degree of ethoxylation of 4 to 20 ethylene oxide units, and also the polyethylene oxide ethers of nonylphenol having a degree of ethoxylation of 4 to 20 ethylene oxide units. Still further examples include copolymers of ethylene oxide and propylene oxide with a minimum content of at least 10% by weight of ethylene oxide.

Preferred emulsifiers are ethoxylated branched or unbranched aliphatic alcohols, particularly having a degree of ethoxylation of 3 to 80 ethylene oxide units and $C_8$ to $C_{36}$ alkyl radicals. Preferred nonionic emulsifiers also include $C_{13}$-$C_{15}$ oxo-process alcohol ethoxylates having a degree of ethoxylation of 3 to 30 ethylene oxide units, and $C_{16}$-$C_{18}$ aliphatic alcohol ethoxylates having a degree of ethoxylation of 11 to 80 ethylene oxide units. Particularly preferred are $C_{12}$-$C_{14}$ aliphatic alcohol ethoxylates having a degree of ethoxylation of 3 to 30 ethylene oxide units, and copolymers of ethylene oxide and propylene oxide with a minimum content of at least 10% by weight of ethylene oxide. Preferably, these surfactants do not contain alkyl phenol ethoxylate structures and are not endocrine disruptors.

The total amount of emulsifier is typically in a range from 0.5 to 5% by weight, preferably 1 to 3% by weight, based in each case on the total weight of the monomers.

Nonionic Protective Colloid

One or more nonionic protective colloid(s) is/are used to stabilize the VAE dispersions during and after the polymerization reaction by which they are formed. Suitable nonionic protective colloids include polyvinyl alcohol (PVOH)

and nonionic cellulose derivatives, for example hydroxyethylcellulose, although others may be used instead or in addition. Other examples include polyvinylpyrrolidone, PVOH bearing ethylene oxide or polyethylene oxide substituents, and acetoacetylated PVOH. In addition, copolymers of PVOH may be used. Examples include ethylene and/or N-vinylpyrrolidone copolymers of vinyl alcohol.

Polyvinyl alcohols are particularly useful. Suitable PVOH's include partially hydrolyzed polyvinyl alcohols having a degree of hydrolysis of 80 to 99 mol %, preferably 85 to 99 mol %, and a viscosity, in 4% strength aqueous solution, of 1 to 30 mPas, preferably 3 to 6 mPas (Hoeppler viscosity, determined at 20° C. in accordance with DIN 53015). Most preferred are polyvinyl alcohols having a degree of hydrolysis in a range from 98 to 99 mol % and a 4% strength aqueous solution viscosity in a range from 3 to 6 mPas. Such PVOH's are commercially available or obtainable by processes known to the skilled person. A single PVOH having the recited degree of hydrolysis may be used, or a combination of two or more PVOH's having different degrees of hydrolysis that in combination have the recited degree of hydrolysis.

The protective colloid or combination of protective colloids, for example polyvinyl alcohol(s), will typically be present at a level of at least 0.1% by weight, or at least 0.2% or 0.5%. Typically, the level will be at most 10%, or at most 5% or 1%. These percentages indicate the amount of protective colloid(s) relative to the total weight of all monomers used for the polymerization.

Emulsion Polymerization Procedure

During polymerization the dispersion is stabilized with one or more nonionic surfactants and one or more protective colloids, for example polyvinyl alcohols. The VAE dispersions stabilized with the combination of nonionic surfactant and protective colloid may be prepared by emulsion polymerization, typically at a temperature in a range from 40° C. to 100° C., more typically 50° C. to 90° C. and most typically 60° C. to 80° C. The polymerization pressure is generally between 40 and 100 bar, more typically between 45 and 90 bar, and may vary particularly between 45 and 85 bar, depending on the ethylene feed.

Polymerization may be initiated using a redox initiator combination such as is customary for emulsion polymerization. Redox initiator systems may be used to prepare VAE dispersions suitable for use according to the invention. The initiators may be formaldehyde-generating redox initiation systems such as sodium formaldehyde sulfoxylate. In some embodiments, however, it is desirable to minimize the formaldehyde level in the dispersion. In such cases, it is desirable to use a non-formaldehyde generating redox initiation system. In general, suitable non-formaldehyde generating reducing agents for redox pairs include, as nonlimiting examples, those based on ascorbic, bisulfite, erythorbate or tartaric chemistries as known in the art, and a commercial reducing agent known as BRUGGOLITE® FF6M manufactured by Bruggeman Chemical of Heilbronn, Germany. Non-redox initiators may also be used, such as peroxides and azo-type initiators, all of which are well known in the art.

All of the monomers may form an initial charge, or all of the monomers may form a feed, or portions of the monomers may form an initial charge and the remainder may form a feed after the polymerization has been initiated. The feeds may be separate (spatially and chronologically), or all or some of the components may be fed after pre-emulsification. Once the polymerization process has ended, post-polymerization may be carried out using known methods to remove residual monomer, one example of a suitable method being post-polymerization initiated by a redox catalyst. Volatile residual monomers may also be removed by distillation, preferably at subatmospheric pressure, and, where appropriate, by passing inert entraining gases, such as air, nitrogen, or water vapor through or over the material.

The solids contents of suitable VAE copolymer dispersions as made are typically in a range from 45 to 75% by weight, but dispersions with other solids levels may be used.

The dispersions typically have a viscosity, if diluted to a 25% solids level, of at least 5 mPas, or at least 10, 20, or 30 mPas. The viscosity will typically be at most 80 mPas, or at most 70, 60, or 50 mPas. The viscosities are determined using a Brookfield Viscometer Model LVD with a #3 spindle at 60 rpm and 25° C.

Fibrous Nonwoven Substrate

The fibrous nonwoven substrate can be a natural fiber such as (but not limited to) cellulose fiber or wood pulp, or a synthetic fiber including but not limited to one or more of polyester, polyethylene, polypropylene and polyvinyl alcohol, or viscose fiber, or a combination of any of these, processed by a dry (airlaid, carded, rando) or wet laid process. The basis weight of the fibrous nonwoven substrate prior to treatment with the nonionic binder composition is typically at least 10 g/m$^2$, or at least 45 g/m$^2$, and is typically at most 150 g/m$^2$, or at most 120 g/m$^2$.

Aqueous Disinfectant Lotion

The aqueous lotion that is absorbed in the bonded nonwoven substrate includes one or more cationic disinfectants. These are typically quaternary ammonium disinfectant compounds. Benzalkonium chloride is one specific example, although any other cationic disinfectant known in the art may be used instead or in addition. Some of the cationic disinfectant may be dissolved in the aqueous phase of the lotion while some is adsorbed on the surface of the fibers of the nonwoven substrate. Preferably, the cationic disinfectant(s) include(s) only one cationic moiety per molecule.

The aqueous lotion may optionally also contain salts that are not cationic disinfectant(s). Salts of any kind may be included, for example organic salts, inorganic salts, and salts comprising an organic anion and a metal, a non-disinfectant quaternary ammonium cation, or a nonquaternary ammonium cation, i.e., $NH_4^+$ or a protonated primary, secondary, or tertiary amine. Nonlimiting examples include acetates, acetylides, ammonium salts (excluding quats), arsenates, astatides, azides, bihalide salts, bicarbonates, bisulfides, borides, borohydrides, borohalides, carbonates, citrates, cyanates, cyanides, formates, germanates, glycinates, halates, halides, hydrides, hydroselenides, hydrosulphides, hydroxides, imides, metaniobates, metaantalates, metavanadates, nitrates, nitrides, nitrites, oxides, perchlorates, phosphates, phosphonium salts, selenides, selenites, selenates, sulphides, sulphates, ternary salts, non-disinfectant tetraalkyl ammonium salts, tellurides, thiocyanates, and/or vanadates. Specific examples include potassium citrate, sodium citrate, sodium tartrate, potassium tartrate, potassium lactate, sodium lactate, salicylate salts of sodium and/or potassium, magnesium sulphate, sodium chloride, ammonium chloride, and/or potassium chloride. However, any one or more of the abovementioned salts, or all salts other than cationic disinfectants, may be excluded.

The aqueous lotion may also comprise an organic solvent which, if present, will typically constitute at most 10% of the lotion composition, or at most 5, 2, or 1%. Examples include $C_{1-6}$ alkanols, $C_{1-6}$ diols, $C_{1-10}$ alkyl ethers of alkylene glycols, $C_{3-24}$ alkylene glycol ethers, and/or polyalkylene glycols. Specific types of solvents include alkanols such as methanol, ethanol, n-propanol, isopropanol, butanol, pentanol, and/or hexanol, and their various positional isomers; acetone; and glycol ethers such as ethylene glycol monopropyl ether, ethylene glycol monobutyl ether, ethylene glycol monohexyl ether, propylene glycol n-propyl ether, propylene glycol monobutyl ether, propylene glycol t-butyl ether, diethylene glycol monoethyl or monopropyl or monobutyl ether, di- or tri-polypropylene glycol methyl or ethyl or propyl or butyl ether, acetate and/or propionate esters of glycol ethers. However, any one or more of the abovementioned solvents, or all solvents, may be excluded.

Making the Antimicrobial Nonwoven Wet Wipe

The nonionic VAE binder composition is typically applied to the nonwoven substrate via spray application, saturation, gravure printing or foaming. The binder composition may optionally include a catalyst, for example an acidic compound or ammonium salt thereof. One example is ammonium chloride.

A wetting additive can be included in the binder composition to aid in the wetting not only of the formulated binder on the substrate, but also of the subsequent finished fibrous nonwoven substrate. The wetting additive should be either a nonionic or cationic type wetting surfactant so as not to reduce the efficacy of the cationic disinfectant added as a lotion to the bound nonwoven substrate. One example is SURFYNOL® 465, a nonionic ethoxylated acetylenic diol sold by Air Products. The wetting agent can be included in the binder composition at a level of 0.1 to 3 dry parts, based on the weight of dry polymer, but is more typically formulated at between 0.5 and 2 parts.

The composition is typically applied at a solids level between 0.5 to 30%, depending on the desired loading on the substrate. Typically, amount of binder on a dry basis will be at least 5%, or at least 10% or 15%, based on the weight of the untreated substrate. It will typically be at most 50%, or at most 40% or 30%.

After the binder composition is applied to the substrate, the substrate is dried. This is typically done at a temperature in a range from 120° C. to 160° C., but higher or lower temperatures may be used. After that the aqueous lotion containing the cationic disinfectant may be applied.

Alternatively, the cationic disinfectant may be included in the VAE binder composition instead of being added separately in the lotion as described above. In that case, water and any other lotion components, for example solvents, can be added to the substrate after the binder composition has been applied and dried, and it is understood that some or all of the cationic disinfectant may dissolve in the water. Or, both modes of adding the cationic disinfectant may be used. In any of these modes, the aqueous lotion will typically be present in an amount of at least 50 parts lotion (wet basis), or at least 150, 200, or 250 parts, per 100 parts bonded substrate (dry basis). The amount of lotion will typically be at most 500 parts, or at most 400 or 350 parts, per 100 parts substrate. In all cases, the resulting wet wipe may be packaged in any way that is effective to minimize or avoid drying out.

EXAMPLES

Measurement of Tg

The glass transition temperature (Tg) of the copolymers was determined by means of differential scanning calorimetry (DSC) using a Mettler-Toledo DSC1 dynamic differential scanning calorimeter with a heating rate of 10° K. per minute according to ASTM D3418-82 as onset temperature. The onset of the glass transition was evaluated in the 2nd heating cycle.

Measurement of Viscosity—Brookfield

Unless otherwise noted, Brookfield viscosities of copolymer dispersions and adhesive compositions were determined using a Brookfield Viscometer Model LVD with a #3 spindle at 60 rpm and 25° C.

Viscosities of polyvinyl alcohols are Hoeppler viscosities of 4% aqueous solutions, determined at 20° C. in accordance with DIN 53015.

The following nonionic vinyl acetate ethylene dispersions co-polymerized with NMA and acrylamide were prepared and tested.

Example 1

The following ingredients were mixed together: 3.200 kg of a 10% aqueous solution of SELVOL® 107 (a poly(vinyl alcohol) with average hydrolysis level of 98-99%, 4% aqueous is solution viscosity of 5.5-6.5 cps, available from Sekisui), 3.200 kg of RHODASURF® TLA 3040 (a 40% solution of a tridecyl alcohol ethoxylate surfactant that has approximately 30 ethylene oxide units per tridecyl alcohol, available from Solvay), 1.600 kg of PLURONIC® F68 (an ethylene oxide/propylene oxide block copolymer, available from BASF Chemical Corp.), 0.640 kg of PLURONIC® L64 (an ethylene oxide/propylene oxide block copolymer, available from BASF Chemical Corp.) and 40.0 g of dibasic ammonium phosphate were dissolved in 27.100 kg of deionized water. The pH of this mixture was adjusted to 3.8 using 40.0 g of phosphoric acid (85%) and 1.7 g of ferrous ammonium sulfate was then added to the mixture. This mixture was added to a thirty five gallon pressure reactor that had been purged with nitrogen, and 54.372 kg of vinyl acetate was added with agitation (350 rpm).

The reactor was purged with ethylene, the agitation was maintained at 350 rpm, and 9.595 kg of ethylene was added to the reactor. The temperature was then increased to 35° C., and 118.0 g of a 4.8% aqueous sodium erythorbate solution (pH adjusted to 4.5 with 85% phosphoric acid) was added to the reactor. The reactor contents were allowed to equilibrate and the pressure at this point was 392 psi. A 4.0% aqueous solution of tert-butyl hydroperoxide and a 4.8 aqueous solution of sodium erythorbate (pH adjusted to 4.5 with 85% phosphoric acid) were continuously fed to the reactor at a rate of 10.0 g/min and 16.7 g/min respectively. After the temperature rose 1° C., the reactor temperature was allowed to increase to 75° C. over 60 minutes. In addition, 11.440 kg of an aqueous solution containing 28% b.w. N-methylolacrylamide and 20% b.w. acrylamide, available under the tradename FLOCRYL® NMA 2820, was fed to the reactor over 180 minutes, and the feed line for the NMA-LF was rinsed to the reactor with an additional 0.375 kg of water. The addition rate for the NMA-LF was approximately constant over this 3 hour delay period.

The flow rates of the tert-butyl hydroperoxide and sodium erythorbate feeds were maintained at an approximately 1:1.7 ratio and the flows were adjusted so that the 75° C. reaction temperature was maintained. The unreacted vinyl acetate was measured during the course of the reaction and found to be 46.6% after 1 h, 26.1% after 2 h, 7.6% after 3 h, and 4.7% after 3.2 h. At the end of 3.5 h, the tert-butyl hydroperoxide and sodium erythorbate feeds were stopped, the reaction was cooled to 50° C. and the reaction mixture was is transferred to a degasser to remove unreacted ethylene. The reactor was rinsed with 2.300 kg of water, which was also transferred to the degasser, and a mixture of 35.0 g of RHODOLINE® DF540 defoamer (available from Solvay) and 110.0 g of water were added to inhibit foam formation. In order to reduce unreacted vinyl acetate monomer below 0.1%, 0.740 kg of an 8.0% aqueous sodium erythorbate solution and 0.740 kg of a 6.30% aqueous tert-butyl hydroperoxide solution were added over 40 minutes. Finally, 18.9 g of dodecylguanidine hydrochloride dissolved in 215 g of a 7.01% aqueous hydrogen peroxide solution was added over 30 minutes.

The final properties of the dispersion were as follows:
Solids: 56.1%
pH: 5.4
Viscosity (60 rpm): 340 cps
Grit:* 35 ppm
Unreacted vinyl acetate: 1752 ppm
Tg (onset): 2.0° C.
* material retained on 100 mesh screen Example 2

The following ingredients were mixed together: 475.0 g of a 2% aqueous solution of NATROSOL® 250GR (hydroxyethylcellulose with a 2% aqueous solution viscosity of 250-450 cps, available from Ashland Chemical Corp.), 95.0 g of RHODASURF® TLA 3040 (a 40% solution of a tridecyl alcohol ethoxylate surfactant that has approximately 30 ethylene oxide units per tridecyl alcohol, available from Solvay), 23.75 g of PLURONIC® F68 (an ethylene oxide/propylene oxide block copolymer, available from BASF Chemical Corp.), 28.5 g of PLURONIC® L64 (an ethylene oxide/propylene oxide block copolymer, available from BASF Chemical Corp.) and 1.0 g of sodium citrate were dissolved in 420.0 g of deionized water. The pH of this mixture was adjusted to 4.0 using 3.31 g of a 50% aqueous solution of citric acid, and 5.0 g of a 1% aqueous solution of ferrous ammonium sulfate was then added to the mixture. This mixture was added to a one gallon stainless steel pressure reactor that had been purged with nitrogen, and 1615 g of vinyl acetate was added with agitation (100 rpm).

The reactor was purged with ethylene, the agitation was increased to 900 rpm, and 285 g of ethylene was added to the reactor. The temperature was then increased to 35° C., and 3.0 g of a 7.2% aqueous sodium erythorbate solution (pH adjusted to 4.5 with 50% phosphoric acid) was added to the reactor. An aqueous solution of 6.0% tert-butyl hydroperoxide and a 7.2% aqueous solution of sodium erythorbate were each continuously fed to the reactor at a rate of 0.2 g/min. After the temperature rose 1° C., the reactor temperature was allowed to increase to 85° C. over 50 minutes. In addition, 339.3 g of an aqueous solution containing 28% b.w. N-methylolacrylamide and 20% b.w. acrylamide, available under the tradename FLOCRYL® NMA 2820, was fed to the reactor over 135 minutes.

The tert-butyl hydroperoxide and sodium erythorbate feeds were maintained at equal flow rates and adjusted so that the 85° C. reaction temperature was maintained. The unreacted vinyl acetate was measured during the course of the reaction and found to be 47.2% after 0.5 h, 14.3% after 1 h, 3.7% after 1.75 h and 0.6% after 2.25 h. At the end of 2.25 h, the tert-butyl hydroperoxide and sodium erythorbate feeds were stopped, the reaction was cooled to 50° C. and the reaction mixture was transferred to a degasser to remove unreacted ethylene. A mixture of 1.0 g of RHODOLINE® DF540 defoamer (available from Solvay) and 5 g of water were added to inhibit foam formation. In order to reduce unreacted vinyl acetate monomer below 0.1%, 20.0 g of a 10% aqueous sodium erythorbate solution and 20.0 g of a 7.0% aqueous tert-butyl hydroperoxide solution were added over 15 minutes.

The final properties of the dispersion were as follows:
Solids: 55.9%
Viscosity (60 rpm): 750 cps
In Grit: 37 ppm
Tg (onset): 2.7° C.

Example 3

The following ingredients were mixed together: 47.5 g of a 10% aqueous solution of SELVOL® 205 (a poly(vinyl alcohol) with average hydrolysis level of 87-89%, 4% aqueous solution viscosity of 5.2-6.2 cps, available from Sekisui), 95.0 g of RHODASURF® TLA 3040 (a 40% solution of a tridecyl alcohol ethoxylate surfactant that has approximately 30 ethylene oxide units per tridecyl alcohol, available from Solvay), 47.5 g of PLURONIC® F68 (an ethylene oxide/propylene oxide block copolymer, available from BASF Chemical Corp.), 19.0 g of PLURONIC® L64 (an ethylene oxide/propylene oxide block copolymer, available from BASF Chemical Corp.) and 1.2 g of sodium citrate were dissolved in 950.0 g of deionized water. The pH of this mixture was adjusted to 4.0 using 3.91 g of a 50% aqueous solution of citric acid, and 5.0 g of a 1% aqueous solution of ferrous ammonium sulfate was then added to the mixture. This mixture was added to a one gallon stainless steel pressure reactor that had been purged with nitrogen, and 1615 g of vinyl acetate was added with agitation (100 rpm).

The reactor was purged with ethylene, the agitation was increased to 900 rpm, and 285 g of ethylene was added to the reactor. The temperature was then increased to 35° C., and 3.0 g of a 4.8% aqueous sodium erythorbate solution was added to the reactor. An aqueous solution of 4.0% tert-butyl hydroperoxide and a 4.8% aqueous solution of sodium erythorbate were each continuously fed to the reactor at a rate of 0.2 g/min. After the temperature rose 1° C., the reactor temperature was allowed to increase to 60° C. over 60 minutes. In addition, 339.3 g of an aqueous solution containing 28% b.w. N-methylolacrylamide and 20% b.w. acrylamide, available under the tradename FLOCRYL® NMA 2820, was fed to the reactor over 135 minutes.

The tert-butyl hydroperoxide and sodium erythorbate feeds were maintained at equal flow rates and adjusted so that the 60° C. reaction temperature was maintained. The unreacted vinyl acetate was measured during the course of the reaction and found to be 36.8% after 1 h, 11.1% after 1.75 h and 4.8% after 2.75 h. At the end of 2.75 h, the tert-butyl hydroperoxide and sodium erythorbate feeds were stopped, the reaction was cooled to 50° C. and the reaction mixture was transferred to a degasser to remove unreacted ethylene. A mixture of 1.0 g of RHODOLINE® DF540 defoamer (a proprietary defoamer available from Solvay) and 5 g of water were added to inhibit foam formation. In order to reduce unreacted vinyl acetate monomer below 0.1%, 20.0 g of a 10% aqueous sodium erythorbate solution and 20.0 g of a 7.0% aqueous tert-butyl hydroperoxide solution were added over 15 minutes.

The final properties of the dispersion were as follows:
Solids: 48.1%
Viscosity (60 rpm): 592 cps
Grit: 236 ppm
Tg (onset): 3.0° C.

Example 4

The following ingredients were mixed together. 3.310 kg of a 10% aqueous solution of SELVOL® 107 (a poly(vinyl alcohol) with average hydrolysis level of 98-99%, 4% aqueous solution viscosity of 5.5-6.5 cps, available from Sekisui), 3.310 kg of RHODASURF® TLA 3040 (a 40% solution of a tridecyl alcohol ethoxylate surfactant that has approximately 30 ethylene oxide units per tridecyl alcohol, available from Solvay), 0.828 kg of PLURONIC® F68 (an ethylene oxide/propylene oxide block copolymer, available from BASF Chemical Corp.) and 0.993 kg of PLURONIC® L64 (an ethylene oxide/propylene oxide block copolymer, available from BASF Chemical Corp.) were dissolved in 28.046 kg of deionized water. The pH of this mixture was adjusted to 4.0 using 63.0 g of citric acid and 1.75 g of ferrous ammonium sulfate was then added to the mixture. This mixture was added to a thirty five gallon pressure reactor that had been purged with nitrogen, and 56.275 kg of vinyl acetate was added with agitation (375 rpm).

The reactor was purged with ethylene, the agitation was maintained at 375 rpm, and 9.930 kg of ethylene was added to the reactor. The temperature was then increased to 35° C., and 105.0 g of a 4.8% aqueous sodium erythorbate solution (pH adjusted to 4.5 with citric acid) was added to the reactor. The reactor contents were allowed to equilibrate and the pressure at this point was 399 psi. A 6.0% aqueous solution of tert-butyl hydroperoxide and a 4.8 aqueous solution of sodium erythorbate (pH adjusted to 4.5 with citric acid) were continuously fed to the reactor at a rate of 6.7 g/min and 6.7 g/min respectively. After the temperature rose 1° C., the reactor temperature was allowed to increase to 85° C. over 60 minutes. In addition, 11.823 kg of a 28.0% active aqueous solution of NMA-LF (FLOCRYL® NMA 2820, an aqueous mix of approximately 28% N-methylolacrylamide and 20% acrylamide, available from SNF Floerger) was fed to the reactor over 150 minutes, and the feed line for the NMA-LF was rinsed to the reactor with an additional 0.375 kg of water. The addition rate for the NMA-LF was approximately constant over this 2.5 hour delay period.

The flow rates of the tert-butyl hydroperoxide and sodium erythorbate feeds were maintained at an approximately 1:1 ratio and the flows were adjusted so that the 85° C. reaction temperature was maintained. The unreacted vinyl acetate was measured during the course of the reaction and found to be 46.2% after 1 h, 32.2% after 2 h, 7.4% after 2.5 h, and 1.9% after 3 h. At the end of 3 h, the tert-butyl hydroperoxide and sodium erythorbate feeds were stopped, the reaction was cooled to 50° C. and the reaction mixture was transferred to a degasser to remove unreacted ethylene. The reactor was rinsed with 2.300 kg of water, which was also transferred to the degasser, and a mixture of 35.0 g of RHODOLINE® DF540 defoamer (available from Solvay) and 110.0 g of water were added to inhibit foam formation. In order to reduce unreacted vinyl acetate monomer below 0.1%, 0.767 kg of a 9.1% aqueous sodium erythorbate solution and 0.767 kg of a 6.40% aqueous tert-butyl hydroperoxide solution were added over 40 minutes. Finally, 17.5 g of dodecylguanidine hydrochloride dissolved in 0.212 kg of deionized water and 0.662 kg of monoammonium phosphate dissolved in 2.000 kg of deionized water were added.

The final properties of the dispersion were as follows:
Solids: 58.1%
pH: 4.7
Viscosity (60 rpm): 904 eps
Grit: 130 ppm
Unreacted vinyl acetate: 401 ppm
Tg (onset): 4.9° C.

Testing and Results:

Testing and measurements to demonstrate the improvement in cationic disinfectant efficacy wet wipe according to the invention was performed as follows.

1. Application of Binder to Nonwoven.

The nonwoven base substrates used in the study were produced via the airlaid process and were made of 88% cellulose fiber and 12% synthetic bi-component fiber comprised of a polyethylene sheath and a polyester core. Basis weight of the base airlaid was about 90 grams/m$^2$. The binders listed in Table 1 were formulated as shown in Table 2 and sprayed onto both sides of the airlaid substrate as a 20% solids aqueous composition to obtain a polymer add-on of 20% (dry on dry substrate) and dried for 3 minutes at 150° C. in a Mathis through air dryer. The bound substrates were placed in a constant temperature and humidity room at 21° C. and 50% relative humidity prior to the application of the quaternary amine. The physical properties of these substrates bound with the binders listed are shown in Table 3. Dry and wet tensile breaking strength testing were performed according to ASTM method D 5035-95.

TABLE 1

| VAE Binder Sample | Surfactant Type | Solids % | pH | Viscosity cps | Tg | Benzalkonium Chloride Efficacy ppm |
|---|---|---|---|---|---|---|
| VINNAPAS ® 192* | anionic | 52.3 | 5.3 | 94 | 8.6 | 25 |
| Example 1 | nonionic | 56.1 | 5.4 | 340 | 1.96 | 117 |
| Example 2 | nonionic | 55.0 | 5.1 | 750 | 2.7 | N/A |
| Example 3 | nonionic | 48.1 | 4.9 | 592 | 3.0 | N/A |
| VINNAPAS ® 192* | anionic | 52.3 | 5.3 | 94 | 8.6 | 14 |
| Example 4 | nonionic | 58.1 | 4.7 | 904 | 4.8 | 133 |

*VINNAPAS ® 192 is a self-crosslinking VAE dispersion stabilized with an anionic surfactant system. Example 4 and the second VINNAPAS ® 192 run used a different nonwoven substrate than the other runs.

The benzalkonium chloride efficacy of Example 1 (nonionic surfactant) was 4.7 times that of the comparative Vinnapas 192® run (anionic surfactant), and Example 1, as measured by quantitative HPLC analytical testing, discussed below. The effect was even greater for Example 4 vs. the second Vinnapas 192® run.

TABLE 2

| Component | Dry Parts |
|---|---|
| VAE | 100 |
| Ammonium chloride | 1 |
| SURFYNOL ® 465 Wetting Agent | 1 |

2. Quaternary Amine Application to Nonwoven Substrate

The nonwoven substrates formed in Step I above were wetted with a 378 ppm benzalkonium chloride (a quaternary amine) aqueous solution at a level of 300% of solution based on the dry weight of the nonwoven substrate. The treated substrates were each placed in a plastic bag and sealed to prevent evaporation. The treated substrates sealed in the bags were allowed to sit for 42 hours, after which the benzalkonium chloride solution was expressed from the wipes into individual brown bottles, which were then capped.

3. Benzalkonium Chloride Analysis.

The benzalkonium chloride solutions expressed from the treated wipes in step 2 were diluted at a 1:10 ratio with deionized water further purified with a commercially available Milli-Q® water purifier. A benzalkonium chloride standard from Sigma-Aldrich was used to prepare aqueous standards. Standard solutions ranging from 0.5 ppm to 45 ppm in concentration were used to create a four-point external linear calibration curve. The square of the correlation coefficient ($R^2$) was 0.999905.

The diluted test benzalkonium chloride solutions were then subjected to high pressure liquid chromatography (HPLC) separation on a Waters Alliance system and a Surfactant Plus column using an acetonitrile/potassium phosphate mobile phase. A Waters PDA detector was used for the peak detection. Area under the peak indicates the amount of benzalkonium chloride present. Results from the analysis are shown in Table 1 above.

4. Physical Strength Measurements of Airlaid Substrate Bound with Nonionic Binder.

The cross direction (CD) wet and dry tensile breaking strength of the treated airlaid nonwoven substrates was measured on an Instron tensile tester using ASTM method D 5035-95.

The bonded substrate was die cut using a 5.1 cm×25.4 cm (2 inches×10 inches) die cutter to prepare samples for tensile strength determination. The strips were placed in the jaws of an Instron mechanical tensile tester. For dry tensile determination the die cut samples were placed vertically into the jaws of the tester and the test is initiated. The tensile tester provides the statistics of the maximum tensile achieved at break. A cross head speed of 15.2 cm/minute (6 inches/minute) was used and a gauge length of 20.3 cm (8 inches) was set for is dry tensile determination. A number of tests were performed and the average calculated and reported.

Wet tensile measurement was determined similarly except that the sample was placed into a Finch Cup apparatus that included a water-filled reservoir. The sample was looped around a metal bar and then dipped into the water and held there for 15 seconds. The tensile test was then initiated. A gauge length of 5.1 cm (2 inches) was used due to the loop effect of the tensile strip. The maximum wet strength was determined by the tensile tester. Several tests were performed and the average was calculated.

The absorption rate of the treated substrates was measured using a Sherwood ATS 600 Sherwood Instruments Absorbency Tester.

The physical properties of the nonwoven substrates bound with the inventive nonionic binders as well as with the anionic commercial binder VINNAPAS® 192 are shown in Table 3 below. The inventive nonionic VAE binders provided properties similar to those obtained with the commercial VAE binder. Vinnapas 192 is commonly used in the airlaid nonwovens industry as a binder providing physical properties needs for airlaid nonwoven wet wipes that are saturated with lotions for various applications.

TABLE 3

| Binder Type | CD Dry Tensile Strength gram/5 cm | CD Wet Tensile Strength grams/5 cm | Absorbency Rate grams/gram/second | Maximum Capacity grams/gram |
|---|---|---|---|---|
| VINNAPAS ® 192 | 3591 | 1814 | 1.00 | 11.5 |
| Example 1 | 3151 | 1860 | 0.74 | 11.1 |
| Example 2 | 3223 | 1710 | 0.49 | 10.29 |
| Example 3 | 3435 | 1899 | 0.83 | 10.88 |
| Example 4 | 3618 | 1794 | 0.57 | 10.27 |

The invention claimed is:

1. An antimicrobial nonwoven wet wipe, comprising:
   i) a fibrous nonwoven substrate bonded with an aqueous cross-linkable VAE polymer dispersion stabilized with one or more nonionic colloidal stabilizers and one or more nonionic surfactants, and
   ii) absorbed in the nonwoven substrate, an aqueous lotion comprising one or more cationic disinfectants,
   wherein no anionic surfactants are present in the antimicrobial nonwoven wet wipe, and wherein the cross-linkable VAE polymer is a copolymer prepared by copolymerizing a monomer mixture comprising vinyl acetate, ethylene, and at least one N-methylol-functional monomer.

2. The antimicrobial nonwoven wet wipe of claim 1, wherein the one or more nonionic colloidal stabilizers include polyvinyl alcohol.

3. The antimicrobial nonwoven wet wipe of claim 1, wherein the one or more nonionic colloidal stabilizers include hydroxyethylcellulose.

4. The antimicrobial nonwoven wet wipe of claim 1, wherein the one or more nonionic surfactants include an ethoxylated acetylenic diol.

5. The antimicrobial nonwoven wet wipe of claim 2, wherein the one or more nonionic surfactants include an ethoxylated acetylenic diol.

6. The antimicrobial nonwoven wet wipe of claim 3, wherein the one or more nonionic surfactants include an ethoxylated acetylenic diol.

7. The antimicrobial nonwoven wet wipe of claim 1, wherein the one or more cationic disinfectants include a quaternary ammonium disinfectant.

8. The antimicrobial nonwoven wet wipe of claim 1, wherein the one or more cationic disinfectants include benzalkonium chloride.

9. A method for producing an antimicrobial nonwoven wet wipe of claim 1, comprising:
   a) applying a first aqueous composition comprising the crosslinkable VAE dispersion stabilized with one or more nonionic colloidal stabilizers and one or more nonionic surfactants to a nonwoven substrate;
   b) drying the composition; and
   c) applying a second aqueous composition to the product of step b);
wherein at least one of the first and second aqueous compositions comprises one or more cationic disinfectants, and wherein the cross-linkable VAE polymer is a copolymer prepared by copolymerizing a monomer mixture comprising vinyl acetate, ethylene, and at least one N-methylol-functional monomer.

10. The method of claim 9, wherein the first aqueous composition comprises one or more of said cationic disinfectants.

11. The method according to claim 9, wherein the second aqueous composition comprises one or more of said cationic disinfectants.

12. The antimicrobial wet wipe of claim 9, wherein the N-methylol-functional monomer comprises N-methylolacryl amide.

13. The antimicrobial wet wipe of claim 1, wherein the monomer mixture further comprises (meth)acrylamide.

14. The antimicrobial wet wipe of claim 1, wherein the fibrous non-woven substrate comprises a natural fiber.

15. The antimicrobial wet wipe of claim 1, wherein the fibrous non-woven substrate comprises a cellulose fiber.

16. The antimicrobial wet wipe of claim 1, wherein the fibrous non-woven substrate is produced by an air laid, carded or rando dry process, or by a wet laid process.

17. The antimicrobial wet wipe of claim 1, wherein the N-methylol-functional monomer comprises N-methylolacrylamide.

\* \* \* \* \*